United States Patent [19]

Hendry et al.

[11] Patent Number: 5,238,947
[45] Date of Patent: Aug. 24, 1993

[54] SYNTHETIC PIPERIDINEDIONES WITH CYTOSTATIC ACTIVITY

[75] Inventors: Lawrence B. Hendry, N. Augusta, S.C.; Chung K. Chu, Athens; Virendra B. Mahesh, Augusta, both of Ga.

[73] Assignees: University of Georgia Research Foundation, Inc., Athens; Stereochemical Genetics, Inc., Augusta, both of Ga.

[21] Appl. No.: 705,015

[22] Filed: May 21, 1991

Related U.S. Application Data

[63] Continuation of Ser. No. 508,839, Apr. 12, 1990, abandoned.

[51] Int. Cl.[5] ............... A61K 31/00; C07D 211/40
[52] U.S. Cl. ............................ 514/328; 546/220
[58] Field of Search ..................... 546/220; 514/328

[56] References Cited

U.S. PATENT DOCUMENTS

| 4,444,890 | 4/1984 | Burzynski | 436/64 |
| 4,461,619 | 7/1984 | Hendry et al. | 434/295 |
| 4,470,970 | 9/1984 | Burzynski | 424/177 |
| 4,558,057 | 10/1985 | Burzynski | 514/328 |
| 4,559,325 | 12/1985 | Burzynski | 514/21 |
| 4,593,038 | 6/1986 | Burzynski | 514/328 |
| 4,668,689 | 5/1987 | Foster et al. | 514/318 |
| 4,705,796 | 11/1987 | Hendry et al. | 514/328 |
| 4,721,710 | 1/1988 | Bernhart et al. | 514/234 |

OTHER PUBLICATIONS

Burzynski, et al., Chem. Abstract 105:164561w (1986).
Burzynski, et al., Chem. Abstract 112:196233b (1990).
Burzynski, et al., Drugs Exptl. Clin. Res. X(8-9), 611-619 (1984).
Burzynski, et al., Drugs Exptl. Clin. Res., Suppl. 1 XII, 11-16 (1986).
Burzynski, Drugs Exptl. Clin. Res., Suppl. 1 XII, 17-24 (1986).
Burzynski, et al., Drugs Exptl. Clin. Res., Suppl. 1 XII, 47-55 (1986).
Burzynski, Drugs of the Future 11(8), 679 (1986).
Lee, et al., Chem. Abstract 107:17352s (1987).
Lehner, et al., Drugs Exptl. Clin. Res., Suppl. 1 XII, 57-72 (1986).
Xu, et al., Chem. Abstract 110:185528j (1989).
Aguirre Ormaza, Vincente, Chem. Abstract 107:39628p (1987).
Clissold, et al., Chem. Abstract 112:158062n (1990).
De, et al., Chem. Abstract 89:179814f (1978).
De, et al., Chem. Abstract 89:197241w (1978).
Hibert, et al., Chem. Abstract 105:24193c (1986).
Knabe, Drug Res. 39(II), 1379 (1989).
Lee, et al., Chem. Abstract 102:105809y (1985).
Otani, et al., Journal of Antibiotics XLII(5), 647 (1989).
Shandala, et al., Chem. Abstract 110:75260h (1989).
Sonoda, et al., Journal of Antibiotics XLL(11), 1607 (1989).
Ashraf, et al., Drugs Exptl. Clin. Res., Suppl 1 XII, 37-45 (1986).
Burzynski, Chem. Abstract 90:37144j (1979).
Burzynski, et al., Chem. Abstract 101:204012u (1984).
Wintrobe, et al.; (Harrison's) Principles of Internal Medicine 7th Ed pp. 577-587, 1974.

Primary Examiner—Marianne M. Cintins
Assistant Examiner—Catherine Scalzo
Attorney, Agent, or Firm—Kilpatrick & Cody

[57] ABSTRACT

The present invention are novel compounds of the formula:

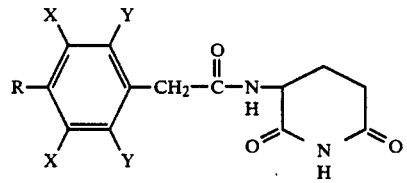

wherein R is OH, NH$_2$, OW, or H; X is H, F, Cl, Br, I, OH, OW, NO$_2$ or NH$_2$; Y is H, F, Cl, I, or Br; W is C(O)Z or a C$_1$ to C$_{12}$ alkyl group; Z is an aliphatic or aromatic group of from C$_1$ to C$_{12}$; X and Y can both vary within the molecule; and if R is H, at least one of X or Y is not H. In a preferred embodiment, R is OH or NH$_2$. The most preferred compound is (4-hydroxy-3-N-phenylacetylamino-2,6-piperidinedione), in which R is OH, X is H and Y is H. These compounds have cytostatic activity and insert stereochemically into DNA.

5 Claims, 3 Drawing Sheets

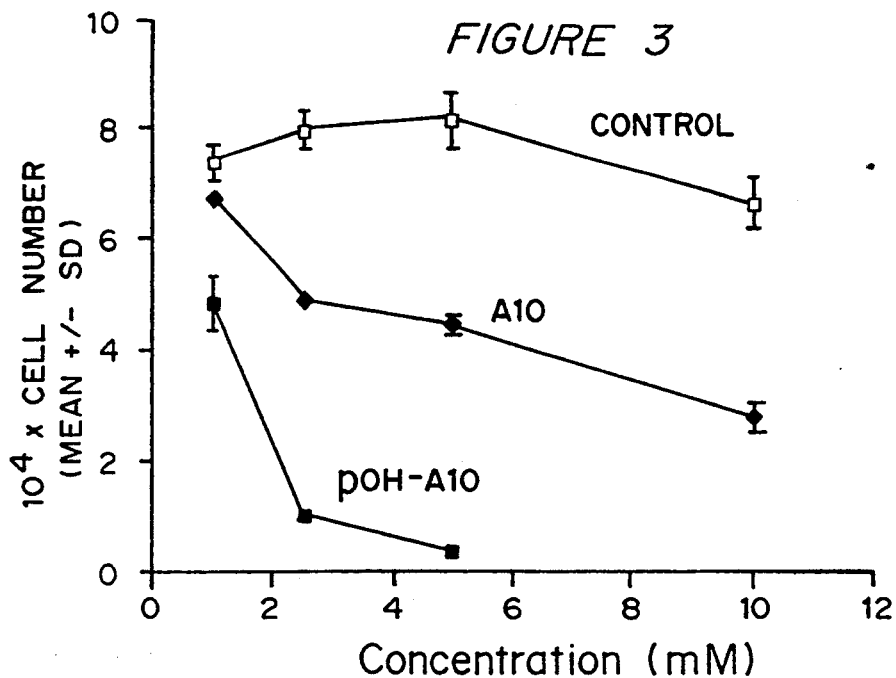
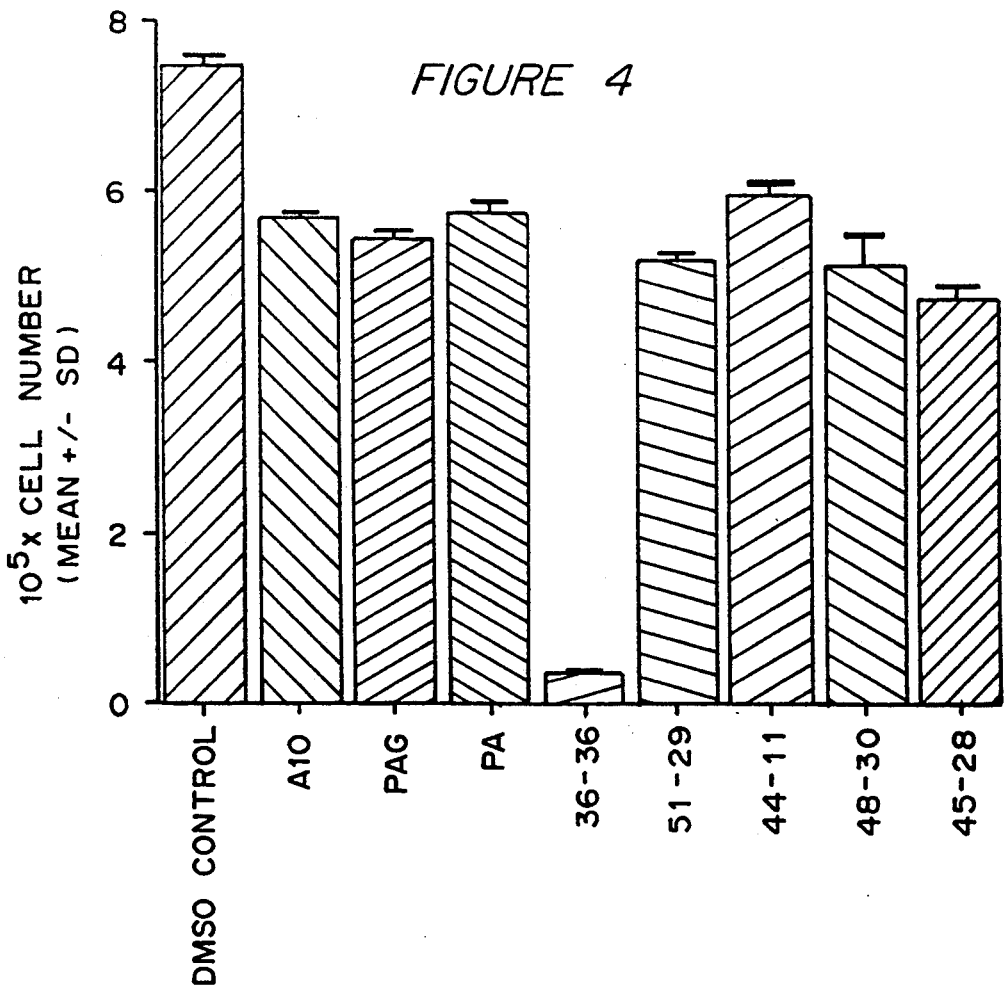

SYNTHETIC PIPERIDINEDIONES WITH CYTOSTATIC ACTIVITY

This application is a continuation of application Ser. No. 07/508,839 filed on apr. 12, 1990, now abandoned.

BACKGROUND OF THE INVENTION

This invention is in the area of synthetic organic chemistry, and specifically relates to new piperidinedione derivatives with cytostatic properties.

A tumor is an unregulated, disorganized proliferation of cell growth. A tumor is malignant, or cancerous, if it has the properties of invasiveness and metastasis. Invasiveness refers to the tendency of a tumor to enter surrounding tissue, breaking through the basal laminas that define the boundaries of the tissues, thereby often entering the body's circulatory system. Metastasis refers to the tendency of a tumor to migrate to other areas of the body and establish areas of proliferation away from the site of initial appearance.

Cancer is now the second leading cause of death in the United States, Europe, and Japan, resulting in approximately 1,000,000 deaths annually in these countries. In the United States alone, each year over one million people are diagnosed with cancer, and over 500,000 people die from the disease. The number of newly diagnosed cancerous growths in patients in the United States is growing at a rate of 3% a year.

Cancer is not fully understood on the molecular level. It is known that exposure of a cell to a carcinogen such as certain viruses, certain chemicals, or radiation, leads to DNA alteration that activates han "oncogene." Oncogenes are initially normal genes (called prooncogenes) that by mutation or altered context of expression become transforming genes. The products of transforming genes cause inappropriate cell growth. More than twenty different normal cellular genes can become oncogenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

All of the various cell types of the body can be transformed into malignant cells. The most frequent tumor site is lung, followed by colorectal, breast, prostate, bladder, pancreas, and then ovary.

Cancer is now treated with one or a combination of three types of therapies: surgery, radiation, and chemotherapy Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia.

Chemotherapy now represents less than 4% of the total expenditures on the treatment of cancer. Chemotherapy involves the disruption of cell replication or cell metabolism. It is used most often in the treatment of leukemia and breast, lung, and testicular cancer.

There are four major classes of chemotherapeutic agents currently in use for the treatment of cancer; anthracyclines, alkylating agents, antiproliferatives, and hormonal agents. A variety of methods exist to attempt to identify new antineoplastic chemotherapeutic agents, including random screening of compounds, preparation of analogs of active compounds, computer or physical modeling, and combinations of these techniques. None of these methods, however, have yet identified the optimal chemotherapeutic agent for neoplastic diseases.

U.S. Pat. No. 4,461,619 to Hendry et al., discloses a method to determine the relationship of chemical structure to biological activity based on the topology and physicochemical properties of "cavities" or "artificial constructs" in double stranded DNA, double stranded RNA, or double stranded DNA-RNA. While modeling can be very helpful in chemotherapy research, it cannot predict whether a target compound will pass through the cell wall, whether it is stable in vivo generally or in the cytoplasm specifically, or whether the therapeutic index is appropriate for clinical use of the drug.

Burzynski has proposed that the human organism is equipped with a corrective system that can reprogram the growth of newly developed neoplastic cells to transform them back into normal cells. He has isolated a number of medium sized peptides, referred to as antineoplastons, that are produced by the body to protect it against the development of neoplastic growth by a nonimmunological process that does not significantly inhibit the growth of normal tissue. The most potent antineoplaston isolated by Burzynski is 3-[N-phenylacetylaminopiperidine]-2,6-dione (referred to below as A10). Antineoplastons are described in U.S. Pat. No. 4,444,890, entitled "Testing Procedure to Aid Diagnosis of Cancer and Evaluate the Progress of Cancer Therapy"; U.S. Pat. No. 4,593,038, entitled "Topical Use of 3-Phenylacetylamino-2,6-Piperidinedione for Treatment of Skin Wrinkles and Hyperpigmentation"; and U.S. Pat. Nos. 4,558,057, 4,559,325 and 4,470,970, entitled "Purified Antineoplaston Fractions and Methods of Treating Neoplastic Disease." According to these patents, administration of antineoplastons to cancer patients has resulted in symptomatic improvement in 93% of the patients treated. A remission of the tumor was noted in about 45% of the patients The initial hydrolysis product and biological degradation product of A10 is phenylacetylglutamine, which is produced in vivo from phenylacetic acid and glutamine. In fact, A10 may be cyclized from phenylacetylglutamine in vivo. Markaverich, et al., report that a compound structurally related to phenylacetic acid, methyl p-hydroxyphenylacetate, inhibits MCF-7 human breast cancer cells in vitro. Markaverich, et al., *J. of Biol. Chem.* 263(15), 7203 (1988).

Hendry has shown that A10 fits in a stereochemical manner between base pairs of double stranded DNA. Hendry, L.B., et al., "Modeling Studies Suggest the Modified Dipeptide Analog Phenylacetylamino-2,6-piperidinedione may interact with DNA," Advances in Experimental and Clinical Chemotheraoy. 15th International Congress of Chemotherapy, Istanbul, Turkey, 1987. Specifically, A10 is capable of forming a stereospecific hydrogen bond between the imino proton of the piperidinedione ring and the phosphate oxygen on the DNA backbone. A10 does not bind covalently to DNA, which may explain why the compound is cytostatic and not cytotoxic. The acute toxicity of A10 in mice is between 1.35 and 10.33 g/kg. AIO has been administered without serious side effects at a dosage of up to 10 grams per day to humans suffering from cancer.

While A10 is a useful drug in the treatment o neoplastic diseases, there is a need for new cytostatic agents that may be more effective in stimulating tumor remission, and that may be effective when administered in lower dosages. The tragic number of deaths that occur each year from this disease accentuates the urgency of this need.

In light of the above, it is clear that there is a strong need for new cytostatic agents that can effectively insert stereochemically into DNA.

Therefore, it is an object of the present invention to provide a compound that has a cytostatic effect on cancer cells.

It is a further object of the present invention to provide a compound that can insert stereochemically into DNA.

SUMMARY OF THE INVENTION

The present invention is a compound with cytostatic activity of the formula:

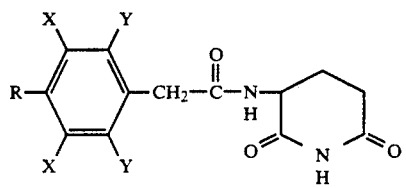

wherein R is OH, $NH_2$, OW, or H; X is H, F, Cl, Br, I, OH, OW, $NO_2$ or $NH_2$; Y is H, F, Cl, I, or Br; W is C(O)Z or a $C_1$ to $C_{12}$ alkyl group; Z is an aliphatic or aromatic group of from $C_1$ to $C_{12}$; X and Y can both vary within the molecule; and if R is H, at least one of X or Y is not H.

In a preferred embodiment, R is OH or $NH_2$. The most preferred compound is (4-hydroxy-3-N-phenylacetylamino-2,6-piperidinedione), in which R is OH, X is H and Y is H.

These compounds exhibit cytostatic activity and inhibit the uptake of radioactive thymidine in a variety of neoplastic cell lines. The preferred compound, 4-hydroxy-3-N-phenylacetylamino-2,6-piperidinedione, has significant cytostatic activity against prolactin stimulated Nb2 lymphoma cells (a T cell derived lymphoma), MCF-7 cells (estrogen sensitive cells), and mouse lymphoma (YAK) cells. "Cytostatic activity" as used herein refers to the ability of a compound to inhibit cell growth or replication. In contrast, "cytotoxic activity" refers to the ability of a compound to kill cells. Cytostatic agents typically cause reversible chemical changes in cells. An example of a reversible change is the formation of anionic bond through ionic bonds. Cytotoxic compounds typically cause irreversible changes in cells. An example of an irreversible change is the formation of a covalent bond.

Modeling studies suggest that 4-hydroxy-3-N-phenylacetylamino-2,6-piperidinedione (referred to below as p-OH-A10) fits easily between base pairs of DNA to form a complex with significantly lower energy than either structure alone. It has now been discovered that the compounds described herein in which R is a proton donating group such as hydroxyl or amino have significantly greater cytostatic effect than A10. Further, it has been discovered that the preferred compounds of this invention are capable of binding to both strands of the DNA, whereas A10 is only capable of binding to one of the strands of DNA. Thymidine uptake studies indicate that the compounds inhibit DNA synthesis.

BRIEF DESCRIPTION OF THE FIGURES

FIG. 3 is a graph indicating the inhibitory effect of 3-[N-4-hydroxyphenylacetylaminopiperidine]-2,6-dione (A10) and 3-[N-phenylacetylaminopiperidine]-2,6-dione (p-OH-A10) on MCF-7 cells growing in log phase.

FIG. 4 is a bar chart graph indicating the inhibition of mouse lymphoma (YAK) cell proliferation by the cytostatic piperidinediones of the present invention (PAG=phenylacetylglutamine; PA=phenylacetic acid). The compound numbers are as indicated in FIG. 2.

DETAILED DESCRIPTION OF THE INVENTION

Figure 1:
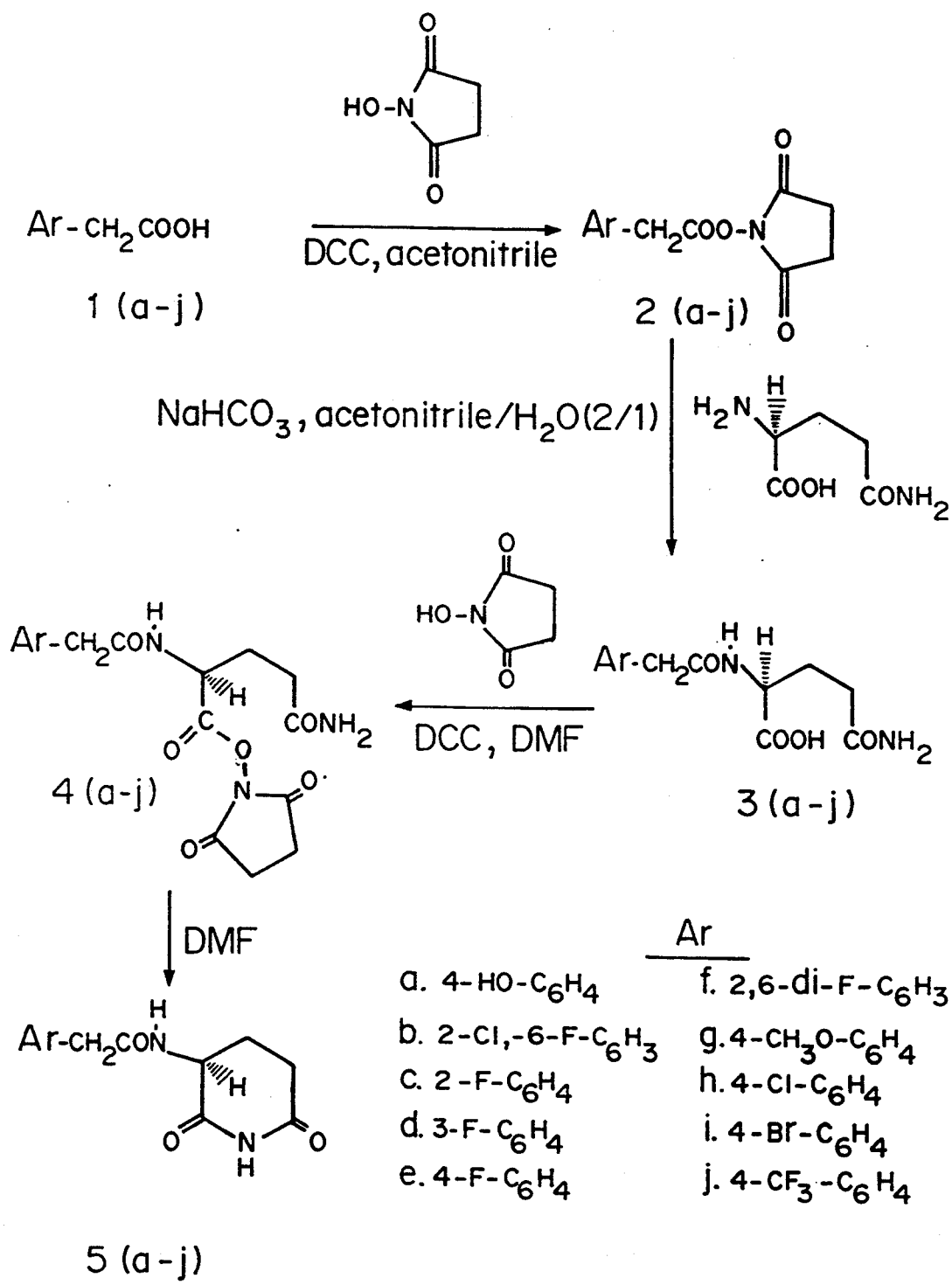
FIG. 1 is a schematic illustrating a method of preparation of the cytostatic piperidinediones of the present invention. The aryl groups in the piperidinedione compounds are abbreviated as follows: a, $4\text{-HO-}C_6H_4$; b, $2\text{-Cl,6-F-}C_6H_3$; c, $2\text{-F-}C_6H_4$; d, $3\text{-F-}C_6H_4$; e, $4\text{-F-}C_6H_4$; f, $2,6\text{-di-F-}C_6H_3$; g, $4\text{-CH}_3\text{O-}C_6H_4$; h, $4\text{-Cl-}C_6H_4$; i, $4\text{-Br-}C_6H_4$; j, $4\text{-CF}_3\text{-}C_6H_4$. The following reagents were used: step (i), N,N-dicyclohexylcarbodiimide (DCC) in acetonitrile; step (ii), $NaHCO_3$ in acetonitrile/$H_2O$ (2/1 ratio); step (iii), DCC in dimethylformamide (DMF); and step (iv), DMF.

The present invention is a compound with cytostatic activity of the formula:

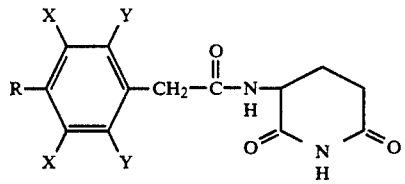

wherein R is OH, $NH_2$, OW, or H; X is H, F, Cl, Br, I, OH, OW, $NO_2$ or $NH_2$; Y is H, F, Cl, I, or Br; W is C(O)Z or a $C_1$ to $C_{12}$ alkyl group; Z is an aliphatic or aromatic group of from $C_1$ to $C_{12}$; X and Y can both vary within the molecule; and if R is H, at least one of X or Y is not H.

Active compounds include 3-[N-4-hydroxyphenylacetylaminopiperidine]-2,6-dione, 3-[N-4-hydroxy-3-fluorophenylacetylaminopiperidine]-2,6-dione, 3-[N-4-hydroxy-3-chlorophenylacetylaminopiperidine]-2,6-dione, 3-[N-3,4-dihydroxyphenylacetylaminopiperidine]-2,6-dione, 3-[N-3-amino-4-hydroxyphenylacetylaminopiperidine]-2,6- dione, 3-[N-4-aminophenylacetylaminopiperidine]-2,6-dione, 3-[N-4-methoxy-3-hydroxyphenylacetylaminopiperidine]-2,6-dione, 3-[N-4-amino-3-fluorophenylacetylaminopiperidine]-2,6-dione, 3-[N-2-fluoro-4-hydroxyphenylacetylaminopiperidine]-2,6-dione, 3-[N-2-fluorophenylacetylaminopiperidine]-2,6-dione, 3-[N-4-acyloxyphenylacetylaminopiperidine]-2,6-dione, and 3-[N-4-alkoxyphenylacetylaminopiperidine]-2,6-dione.

In a preferred embodiment, the active compound has a proton donating group (such as hydroxyl or amino) in the 4-position of the aromatic ring and an electron withdrawing or proton donating group in the 3-position of the aromatic ring. The 2-position of the aromatic ring is preferably unsubstituted (Y=H) or substituted with a small group that does not hinder free rotation of the aromatic ring.

These compounds are synthetic derivatives of the naturally occurring antineoplaston, A10. It has been demonstrated through thymidine incorporation studies that A10 significantly inhibits DNA synthesis (16% at 20 hours; 30% at 40 hours, $p<0.01$). Modeling has indicated that A10 can insert into DNA and form a stabilizing hydrogen bond through its imide group to a phosphate oxygen on one strand of the double stranded DNA.

It has been now been established through thymidine studies that the compounds described herein also significantly inhibit DNA synthesis. Further, it has been discovered that the novel compounds described herein that have a proton donating group, such as hydroxyl or amino, in the 4-position of the aromatic ring have significantly more cytostatic activity than those piperidinedione compounds without proton donating groups in these positions. It is postulated that the increased activity is due to the ability of the proton donating group at the 4-position of the molecule to form a stabilizing stereospecific hydrogen bond with a phosphate oxygen on the nucleic acid strand opposite to that hydrogen bonded to the imide group of the synthetic piperidinedione. These active compounds thus appear to be capable of securing themselves to both strands of DNA in the double helix, resulting in a complex of significantly lower energy than a complex of double stranded DNA with an piperidinedione that is capable of hydrogen bonding to only one strand of the helix, such as A10. As a result, these compounds are expected to have greater therapeutic efficacy and lower toxicity than A10.

Cytostatic agents are useful to moderate the growth of proliferative cells such as neoplastic cells in cell culture or animal models for purposes of research in the area of proliferative diseases. Cytostatic agents are also useful in the study of the bonding patterns and consequent activity of ribonucleic acids. Cytostatic agents may also have a pharmaceutical use as antineoplastic agents in vivo.

The present invention will be further understood with reference to the following non-limiting examples describing the synthesis, activity, and preparation of pharmaceutical compositions of these compounds.

I. Method of Preparation of Cytostatic Piperidinediones

The cytostatic piperidinedione derivatives can be prepared by condensation of the appropriate phenylacetic acid derivative with L-glutamine to produce the corresponding phenylacetylglutamine derivative, that is then intramolecularly cyclized to the desired 3-(N-phenylacetylamino)-2,6-piperidinedione. The condensation reaction is facilitated by prior activation of the phenylacetic acid derivative with a reagent such as N-hydroxysuccinimide in the presence of DCC (N,N-dicyclohexylcarbodiimide), 2-mercaptothiazoline in the presence of DCC, or DCC alone. The phenylacetylglutamine derivative is also preferably activated before cyclization by reaction with N-hydroxysuccinimide in the presence of DCC or by reaction with 1,1'-carbonyldiimidazole. These reactions are described in more detail in Burzynski, *Drugs of the Future*, 10(2), 1003 (1985).

Desired derivatives of phenylacetic acid can be purchased commercially or prepared synthetically by methods known to those skilled in the art according to well established rules of electrophilic and nucleophilic aromatic substitution. For example, 4-hydroxyphenylacetic acid, which is commercially available from Aldrich Chemical Company, Inc., can be nitrated with dilute $HNO_3$ to produce 4-hydroxy-3-nitrophenylacetic acid, that is used as is in the next step of reaction. Alternatively, the nitro group in 4-hydroxy-3-nitrophenylacetic acid can be reduced to the corresponding amine and then reacted with sodium nitrite in acid to form the diazonium salt, that can be converted into a wide range of functional groups, including chloro (CuCl), fluoro ($HBF_4$), bromo (CuBr) and hydroxyl ($H_2SO_4$). Phenylacetic acid can alternatively be nitrated in the 4-position to produce 4-nitrophenylacetic acid, that is used as is in the reaction or converted to the diazonium salt and derivatized. The nitro group can be reduced to the corresponding amino group as a final step of reaction by methods known to those skilled in the art, including catalytic hydrogenation with palladium on carbon.

Prodrugs of the hydroxyl or amino derivatives of 3-N-phenylacetylamino-2,6-piperidinedione can be prepared by alkylation or acylation of the hydroxyl or amino moieties according to established methods. These protecting groups can be cleaved in vivo or in vitro by the appropriate enzyme, generating the active compound.

In FIG. 1, a general reaction scheme is illustrated for the preparation of the cytostatic piperidinediones. As shown, the substituted phenylacetic acids 1 were reacted with N-hydroxysuccinimide to produce the corresponding N-hydroxysuccinimide esters 2, that were reacted with L-glutamine to form the phenylacetylglutamine derivatives 3. Compound 3 was then reacted with N-hydroxysuccinimide and cyclized to form the substituted 3-N-phenylacetylamino-2,6-piperidinedione derivatives 5. Detailed experimental procedures are provided in Examples 1-4. (The numbering scheme for the compounds described in these Examples is specified in FIG. 1.) Physical and NMR data for the N-hydroxysuccinimide esters of substituted phenylacetic acids are provided in Tables 1 and 2, respectively. NMR data for the substituted phenylacetyl-L-glutamines and substituted-3-N-phenylacetylamino-2,6-piperidinediones are provided in Tables 3 and 4, respectively.

In the following working examples, melting points were determined on a Thomas Hoover capillary apparatus and are uncorrected. $^1N$ NMR spectra were recorded on a JEOL FX 90Q fourier transform spectrometer for the 90-MHz $^1H$ NMR spectra, using $Me_4Si$ as internal standard: chemical shifts are reported in parts per million ($\delta$) and signals are quoted as s (singlet), d (doublet), t (triplet), q (quartet), or m (multiplet). UV spectra were obtained on a Beckman DU-7 spectrophotometer. Thin layer chromatography was performed on Uniplates (silica gel) purchased from Analtech Co. Elemental analyses were performed by Atlantic Microlab Inc., Norcross, GA or Galbrait Laboratories, Inc., Knoxville, Tenn.

TABLE 1

Physical Constants and Microanalysts of Compounds

| Compd. (Overall yield) | $\lambda_{max}$ mp °C. | UV(nm) (CH$_3$OH) | Formula | Calcd./ Anal. | % C Calcd./ Found | % H Calcd./ Found | % N Calcd./ Found | % F Calcd./ Found | % Cl Calcd./ Found | Br % Found |
|---|---|---|---|---|---|---|---|---|---|---|
| 2a | 138–140 | | C$_{12}$H$_{11}$NO$_5$ | C, H, N | 57.83 57.90 | 4.45 4.46 | 5.62 5.58 | | | |
| 2b | 109.5–111 | | C$_{12}$H$_9$FClNO$_4$ | C, H, N | 50.45 50.55 | 3.18 3.23 | 4.90 4.83 | | | |
| 2c | 95–96 | | C$_{12}$H$_{10}$FNO$_4$ | C, H, N | 57.37 57.22 | 4.01 3.99 | 5.58 5.53 | | | |
| 2d | 90–91.5 | | C$_{12}$H$_{10}$FNO$_4$ | C, H, N | 57.37 57.45 | 4.01 4.00 | 5.58 5.58 | | | |
| 2e | 100.5–101.5 | | C$_{12}$H$_{10}$FNO$_4$ | C, H, N | 57.37 57.26 | 4.01 4.03 | 5.58 5.59 | | | |
| 2f | 110–111 | | C$_{12}$H$_9$F$_2$NO$_4$ | C, H, N | 53.54 53.56 | 3.37 3.41 | 5.20 6.19 | | | |
| 2g | 108.5–109.5 | | C$_{13}$H$_{13}$NO$_5$ | C, H, N | 59.31 59.22 | 4.98 4.99 | 5.32 5.30 | | | |
| 2h | 135–136 | | C$_{12}$H$_{10}$ClNO$_4$ | C, H, N, Cl | 53.84 53.94 | 3.77 3.76 | 5.33 5.19 | | 13.24 13.18 | |
| 2i | 139–141 | | C$_{12}$H$_{10}$BrNO$_4$ | C, H, N, Br | 46.17 46.22 | 3.23 3.24 | 4.49 4.42 | | | 25.60 25.66 |
| 2j | 120–121 | | C$_{13}$H$_{10}$F$_3$NO$_4$ | C, H, N, F | 51.84 52.16 | 3.35 3.33 | 4.65 4.49 | 18.92 18.72 | | |
| 5a (17.1%) | 172–174 | 229 | C$_{13}$H$_{14}$N$_2$O$_4$ | C, H, N | 59.53 59.45 | 5.38 5.43 | 10.68 10.67 | | | |
| 5b (42.5) | 203–204.5 | 216 | C$_{13}$H$_{12}$FClN$_2$O$_3$ | C, H, N | 52.27 52.37 | 4.05 4.06 | 9.38 9.29 | | | |
| 5c (26.5) | 185–188.5 | 212.5 | C$_{13}$H$_{13}$FN$_2$O$_3$ | C, H, N | 59.08 59.19 | 4.97 4.95 | 10.60 10.51 | | | |
| 5d (20.3) | 180–181 | 209.7 | C$_{13}$H$_{13}$FN$_2$O$_3$ | C, H, N | 59.08 59.16 | 4.97 4.99 | 10.60 10.55 | | | |
| 5e (21.5) | 190–191 | 210 | C$_{19}$H$_{13}$FN$_2$O$_3$ | C, H, N | 59.08 59.03 | 4.96 5.01 | 10.60 10.62 | | | |
| 5f (38.5) | 188–189 | 212.5 | C$_{13}$H$_{12}$F$_2$N$_2$O$_3$ | C, H, N | 55.32 55.24 | 4.29 4.30 | 9.93 9.90 | | | |
| 5g (32.9) | 193–194 | 227.9 | C$_{14}$H$_{16}$N$_2$O$_4$ | C, H, N | 60.85 60.86 | 5.85 5.87 | 10.14 10.20 | | | |
| 5h (40.3) | 207.5–208.5 | 225 | C$_{13}$H$_{13}$ClN$_2$O$_3$ | C, H, N, Cl | 55.62 55.66 | 4.68 4.66 | 9.98 9.93 | | 12.63 12.69 | |
| 5i (40.7) | 213–214 | 228.9 | C$_{13}$H$_{13}$BrN$_2$O$_3$ | C, H, N, Br | 48.02 47.92 | 4.04 4.07 | 8.62 8.57 | | | 24.57 24.67 |
| 5j (41.8) | 177–178 | 227 | C$_{14}$H$_{13}$F$_3$N$_2$O$_3$ | C, H, N, F | 53.60 53.50 | 4.18 4.07 | 8.92 8.84 | 18.14 18.69 | | |

TABLE 2

$^1$H-NMR Signals Observed for N-Hydroxysuccinimide Esters of Substituted Phenylacetic Acids (2a–2j)
(δ ppm downfield from TMS, in DMSO-d$_6$)

| Compd. | Aromatic H | Other Signals |
|---|---|---|
| 2a | 6.95(4H, d-d, J=8.5, 35.7Hz) | 2.79(4H, s, COCH$_2$CH$_2$CO), 3.92(2H, s, CH$_2$COO), 9.38(1H, s, OH) |
| 2b | 7.40(3H, m) | 2.80(4H, s, COCH$_2$CH$_2$CO), 4.22(2H, d, J=1.47Hz, CH$_2$COO) |
| 2c | 7.13–7.55(4H, m) | 2.80(4H, s, COCH$_2$CH$_2$CO), 4.15(2H, s, CH$_2$COO) |
| 2d | 7.05–7.55(4H, m) | 2.81(4H, s, COCH$_2$CH$_2$CO), 4.17(2H, s, CH$_2$COO) |
| 2e | 7.08–7.48(4H, m) | 2.81(4H, s, COCH$_2$CH$_2$CO), 4.12(2H, s, CH$_2$COO) |
| 2f | 7.08–7.56(3H, m) | 2.81(4H, s, COCH$_2$CH$_2$CO), 4.16(2H, s, CH$_2$COO) |
| 2g | 7.09(4H, d-d, J=7.03, 22.27Hz) | 2.80(4H, s, COCH$_2$CH$_2$CO), 3.74(3H, s, OCH$_3$), 4.00(2H, s, CH$_2$COO) |
| 2h | 7.41(4H, m) | 2.81(4H, s, COCH$_2$CH$_2$CO), 4.14(2H, s, CH$_2$COO) |
| 2i | 7.44(4H, d-d, J=8.21, 24.31Hz) | 2.28(4H, s, COCH$_2$CH$_2$CO), 4.12(2H, s, CH$_2$COO) |
| 2j | 7.67(4H, d-d, J=8.49, 15.82Hz) | 2.81(4H, s, COCH$_2$CH$_2$CO), 4.23(2H, s, CH$_2$COO) |

TABLE 3

$^1$H-NMR Signals Observed for (Substituted Phenylacetyl)-L-Glutamine
(δ ppm downfield from TMS, in DMSO-d$_6$)

| Compd. | Aromatic H | ArCH$_2$CON | Other Signals |
|---|---|---|---|
| 3a | 6.85(4H, d-d, J=8.8, 32.2Hz) | 3.31(2H, s) | 2.41(4H, s, CH$_2$CH$_2$), 3.46(1H, b, NCH(CH$_2$CH$_2$)COOH), 3.80(1H, b, CONH), 7.20(1H, s, COOH), 7.28(1H, s, OH), 7.40(2H, s, CONH$_2$) |
| 3b | 7.12–7.58(3H, m) | 3.71(2H, s) | 2.50(4H, s, CH$_2$CH$_2$), 3.45(1H, b, NCH(CH$_2$CH$_2$)COOH), 3.85(1H, b, CONH), 6.59(2H, b, CONH$_2$), 12.27(1H, b, COOH) |
| 3d | 7.03–7.55(4H, m) | 3.52(2H, s) | 1.95(2H, s, CH$_2$CH$_2$), 2.41(2H, s, CH$_2$CH$_2$), 3.24(1H, b, NCH(CH$_2$CH$_2$)COOH), 3.80(1H, b, CON 6.60(2H, b, CONH$_2$), 7.65(1H, b, COOH) |
| 3g | 7.00(4H, d-d, J=7.62, 30.18Hz) | 3.38(2H, s) | 1.92(2H, m, CH$_2$CH$_2$), 2.49(2H, m, CH$_2$CH$_2$), 3.74(3H, s, OCH$_3$), 3.77 |

TABLE 3-continued

1H-NMR Signals Observed for (Substituted Phenylacetyl)-L-Glutamine
(δ ppm downfield from TMS, in DMSO-$d_6$)

| Compd. | Aromatic H | ArCH$_2$CON | Other Signals |
|---|---|---|---|
| 3h | 7.31(4H, m) | 3.47(2H, s) | (1H, m, NCH(CH$_2$CH$_2$)COOH), 6.55(2H, m, CONH2), 7.33(1H, d, J=7.03, CONH), 7.37(1H, m, COOH) 2.01(4H, b, CH$_2$CH$_2$), 4.10(1H, m, NCH(CH$_2$CH$_2$)COOH), 6.74(2H, m, CONH$_2$), 7.30(1H, m, COOH), 8.35(1H, m, CONH) |
| 3i | 7.34(4H, d-d, J=8.21, 23.73Hz) | 3.45(2H, s) | 1.91(4H, b, CH2CH$_2$), 4.13(1H, m, NCH(CH$_2$CH$_2$)COOH), 6.74(2H, m, CONH$_2$), 7.43(1H, m, COOH), 8.42(1H, m, CONH) |
| 3j | 7.57(4H, d-d, J=8.20, 16.7Hz) | 3.59(2H, s) | 1.97(4H, b, CH$_2$CH2), 4.15(1H, m, NCH(CH$_2$CH$_2$)COOH), 6.75(2H, s, CONH$_2$), 7.26(1H, m, COOH), 8.44(1H, m, CONH) |

TABLE 4

1H-NMR Signals Observed for Substituted-3-N-Phenylacetyl-Amino-2,6-Piperidinedione (5a-5j)
(δ ppm downfield from TMS, in DMSO-$d_6$)

| Compd. | Aromatic H | ArCH$_2$CON | CONH-ring | (CH$_2$CH$_2$)CH*CO | CH$_2$CH$_2$ | ring-NH | Other Signal |
|---|---|---|---|---|---|---|---|
| 5a | 6.88(4H, d-d, J=8.9, 32.2Hz) | 3.37(2H, s) | 8.28(1H, d, J=9Hz) | 4.36(1H, q, J=9Hz) **4.49(1H, t, J=9Hz) | 1.85(2H, m) 2.50(2H, m) | 9.20(1H, s) | 10.75(1H, s, OH) |
| 5b | 7.30(3H, m) | 3.20(2H, s) | 8.46(1H, d, J=8.2Hz) | 4.50(1H, q, J=8.2Hz) **4.53(1H, t, J=8.2Hz) | 1.95(2H, m) 2.55(2H, m) | 10.80(1H, s) | |
| 5c | 7.22(4H, m) | 3.56(2H, s) | 8.43(1H, d, J=9.3Hz) | 4.54(1H, q, J=9.3Hz) **4.52(1H, t, J=9.3Hz) | 1.93(2H, m) 2.50(2H, m) | 10.79(1H, s) | |
| 5d | 7.20(4H, m) | 3.52(2H, s) | 8.46(1H, d, J=8.2Hz) | 4.56(1H, q, J=8.2Hz) **4.52(1H, t, J=8.2Hz) | 1.94(2H, m) 2.57(2H, m) | 10.80(1H, s) | |
| 5e | 7.21(4H, m) | 3.45(2H, s) | 8.41(1H, d, J=7.9Hz) | 4.54(1H, q, J=7.9Hz) **4.53(1H, t, J=7.9Hz) | 1.92(2H, m) 2.70(2H, m) | 10.79(1H, s) | |
| 5f | 7.18(3H, m) | 3.58(2H, s) | 8.47(1H, d, J=8.0Hz) | 4.53(1H, q, J=8.0Hz) **4.50(1H, t, J=8.0Hz) | 1.93(2H, m) 2.45(2H, m) | 10.80(1H, s) | |
| 5g | 7.02(4H, d-d, J=8.79, 31.34Hz) | 3.40(2H, s) | 8.32(1H, d, J=7.91Hz) | 4.53(1H, q, J=7.91Hz) **4.52(1H, t, J= 7.91Hz) | 1.91(2H, m) 2.54(2H, m) | 10.77(1H, s) | 3.72(3H, s, OCH$_3$) |
| 5h | 7.33(4H, s) | 3.49(2H, s) | 8.42(1H, d, J=7.91Hz) | 4.55(1H, q, J=8.01Hz) **4.52(1H, t, J= 7.95Hz) | 1.90(2H, m) 2.54(2H, m) | 10.78(1H, s) | |
| 5i | 7.32(4H, d-d, J=8.50, 23.43Hz) | 3.47(2H, s) | 8.43(1H, d, J=8.21Hz) | 4.53(1H, q, J=8.6Hz) **4.51(1H, t, J=8.6Hz) | 1.91(2H, m) 2.54(2H, m) | 10.79(1H, s) | |
| 5j | 7.58(4H, d-d, J=8.49, 15.86Hz) | 3.62(2H, s) | 8.50(1H, d, J=7.91Hz) | 4.54(1H, q, J=7.95Hz) **4.55(1H, t, J=7.95Hz) | 1.92(2H, m) 2.54(2H, m) | 10.79(1H, s) | |

**after exchanged with D$_2$O

Example 1:

General Procedure for the Preparation of N-Hydroxysuccimide Esters of substituted Phenylacetic Acids.

The following is a detailed description for the preparation of the N-hydroxysuccinimide ester of 2-chloro-6-fluorophenylacetic acid 2b. The compounds 2a, 2c-2j were prepared as described below from the appropriate substituted phenylacetic acids (1a, 1c-1j), respectively.

A solution of N-hydroxysuccinimide (5 g, 42 mmol) in 30 mL of anhydrous acetonitrile (dried over 4 Å molecular sieve) was mixed with a solution of 2-chloro-6-fluoro-phenylacetiC acid (1b, 7.92 g, 42 mmol, purchased from Aldrich Chemical Company, Inc., in 50 mL of anhydrous acetonitrile. The clear solution was cooled in an ice bath and N,N-dicyclohexylcarbodiimide (8.66 g, 42 mmol) in 50 mL of anhydrous acetonitrile was added to the mixture with stirring. The reaction mixture was stirred at ambient temperature for 23 hours, until thin layer chromatography indicated the disappearance of the starting material (ethyl acetate/hexanes, 1/1). The colorless precipitate obtained (dicyclohexylurea) was filtered off. The filter cake was washed with acetonitrile and the combined filtrate was then evaporated under vacuum to give a colorless solid (2b, 12.57 g) that was used for next reaction without further purification. Analytical samples were prepared by preparative thin layer chromatography using ethyl acetate/hexanes (1/1).

Example 2:

General Procedure for the Preparation of Substituted Phenylacetyl-L-Glutamines.

To a solution of the N-hydroxysuccimide ester of 2-chloro-6-fluoro-phenyl acetic acid (2b, 12.5 g, 42 mmol) in 120 mL of acetonitrile was added a solution of L-glutamine (6.14 g, 42 mmol) in a mixture of 170 mL of water and 340 mL o acetonitrile containing sodium bicarbonate (7 g, 84 mmol). The mixture was stirred at ambient temperature for 24 hours. The organic layer was separated, and the aqueous layer then extracted with 100 mL acetonitrile. The combined organic layer was evaporated under vacuum to give 3b (15.3 g) as colorless solid. A small amount of the sample was purified by thin layer chromatography (chloroform/methanol, 10.1) for spectroscopic characterization.

The compounds of 3a, 3c-3j were prepared as described above from 2a, 2c-2j, respectively.

Example 3:

General Procedure for the Preparation of N-Hydroxysuccinimide Esters of (Substituted Phenylacetyl)-L-Glutamine.

A solution of N-hydroxysuccinimide (5 g, 42 mmol) in 50 mL of anhydrous dimethylformamide (dried over 4Å molecular sieve) was added to the solution of 2- chloro-6-fluoro-phenylacetyl-L-glutamine (3b, 15.3 g, 42 mmol) in 300 mL of anhydrous DMF. N,N-Dicyclohexylcarbodiimide (8.66 g, 42 mmol) was added to the mixture with stirring. The mixture was stirred at 80° C. for 6 hours and then stirred at ambient temperature for 18 hours. The colorless precipitate obtained was filtered off and the filtrate then used directly in the procedure of Example 4 without isolation of the product. A small amount of sample (4b) was purified by thin layer chromatography (chloroform.methanol, 1/1) for spectroscopic characterization.

The compounds 4a, 4c–4j were prepared at room temperature as described above from 3a, 3c–3j, respectively.

Example 4:

General Procedure for the Preparation of Substitute-3-N-Phenylacetylamino-2,6-Piperidinedione The filtrate obtained in Example 3 (4b) was heated at 95°–100° C. for 6 hours with stirring, during which time a colorless precipitate formed. The mixture was cooled and the precipitate filtered off. The filtrate was stored in the refrigerator overnight. Needle-like crystals that formed were filtered off. The filtrate was then concentrated under vacuum at 60° C. to give a syrup that was recrystallized from hot methanol to provide 5b as a colorless crystal (5.3 g, overall yield 42.5%).

Compounds 5c–5j were prepared as described above from 4c–4j, respectively. However, 5a was purified by a vacuum fresh column chromatography of the syrup using chloroform/methanol (10/1) as the eluent, to get a pale yellow crystal.

II. Activity of Cytostatic Piperidinediones

The Cytostatic activities of the active piperidinediones were tested in three cell lines: prolactin sensitive cells (Nb2 lymphoma cells), estrogen sensitive cells (MCF-7), and cells that are not hormone sensitive (YAK mouse lymphoma cells). In all three cell lines, the preferred compound, p-OH-A10, dramatically inhibited cell growth in a dosedependent fashion. The other piperidinedione derivatives also significantly inhibited cell growth as a function of concentration.

Example 5

Inhibition of Prolactin Stimulated Nb2 Lymphoma Cells

The rat Nb2 lymphoma cell line, a T-cell derived lymphoma, has a specific requirement of lactogenic hormones for growth and provides a useful system to determine the effect of the active compounds on hormone-dependent neoplasia. When Nb2 lymphoma cells are cultured in media containing fetal calf serum (FCS) and horse serum (HS), they demonstrate a doubling time of approximately 15 hours. If, however, the cells are cultured in media devoid of FCS (lactogen source), they enter into a quiescent state of growth. Upon addition of exogenous prolactin (PRL), the cells resume proliferation in a dose-dependent manner. Additionally, it has been demonstrated that interleukin-2 (IL-2) and phorbol esters have mitogenic effects in this cell line.

Antineoplaston A10 (3-phenylacetylamino-2,6-piperidinedione) was a generous gift from the Burzynski Research Institute (Stafford, TX). The A10 analogs were obtained by the synthetic scheme illustrated in FIG. 1. Samples of A10 were analyzed for chemical composition, purity and stability. Analyses were routinely performed on sample solutions dissolved in dimethylformamide using a Finnigan 4023 computerized gas chromatograph-mass spectrometer under the following conditions: injector, 300° C.; source, 300° C.; oven, 265° C. isotherm al; DB5 30 M capillary column; electron energy, 70 ev; scan range, 35–450 amu. In each case, the results showed a single chromatographic peak with the same electron impact mass spectrum. The mass spectral fragmentation pattern was consistent with 3-phenylacetylamino-2,6-piperidinedione (A10) (m/e 246, M+; 155, M+ $-C_7H_7$; 127; 118; 110; 99; 91, $C_7H_7+$; 84; 65; 56). While the mass spectrum of A10 was not present in the computer library, a search revealed an expected close match for the hydrolysis product of A10, 3-N-phenylacetylglutamine. No discernable impurities were detected using reconstructed ion chromatograms and the ion chromatograms of the major diagnostic ions (m/e 246, 155, and 91) possessed single superimposable chromatographic peaks. The retention times and mass spectra obtained in all cases were consistent with those previously reported for A10 as well as those obtained from authentic samples.

Penicillin/streptomycin, FCS, and Fischer's media were obtained from Gibco Laboratories (Grand Island, N.Y.). HS was purchased from MA Bioproducts (Walkersville, Md.). Rat prolactin (rPRL-RP3) was supplied by NIAMDD of the National Institute of Health. Tissue culture flasks (75 cm$^2$), 24- and 96-well plates were obtained from Fisher (Pittsburgh, Pa.).

Nb2 rat lymphoma cells were maintained in suspension cultures in 75 cm$^2$ tissue culture flasks in Fischer's media supplemented with 5% horse serum (HS), 5% fetal calf serum (FCS), $10^{-4}$M 2-mercaptoethanol, 50 units/ml penicillin, 50 µg/ml streptomycin, in an atmosphere of 5% $CO_2$; 95% air at 37° C.

The proliferation of NB2 lymphoma cells was determined by the following procedure. The cells were centrifuged (300 x g, 4 minutes), washed three times in media containing only HS, and then resuspended in the same media. Cells were then cultured for 24 hours prior to use, at which time prolactin and test compound were added. For cell counting, 100 µl aliquots of cells were added to 10 ml of isoton (Coulter Counter Electronics); the cell number was determined in a Coulter counter (model ZM). All experiments were performed in triplicate.

The final concentration of test compound in the culture system was 1 mg/ml. Approximately 5 mg of each of the compounds were weighed and dissolved in heated DMSO (40° C.) to give an equivalent concentration of 200 mg/ml. An equal volume of heated 95% ethanol was added to each compound to give a 100 mg/ml equivalent followed by a 1:50 dilution in Fischer's media containing 5% horse serum, pen/strp, and 2-mercaptoethanol (A10 and analog concentration - 2 mg/ml). The least soluble compound was the parent A10. It was noted that p-OH-A10 had a yellow appearance. A volume of 400 µl of cells containing solvent were added. Following a 48 hour culture, cell counts were made.

Figure 2:
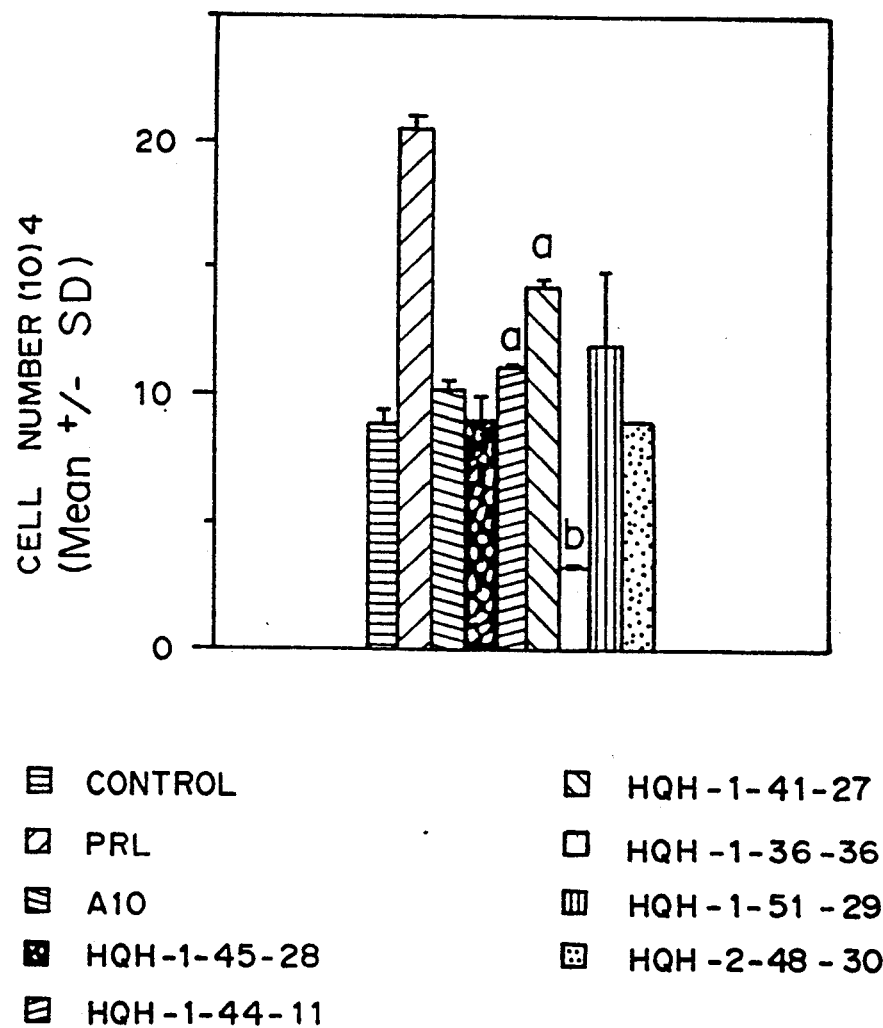
FIG. 2 is a bar chart graph indicating the inhibition of prolactin stimulated Nb2 lymphoma cell growth by cytostatic piperidinediones. Equivalent amounts (1 mg/ml) of A10 or A10 analogs were introduced simultaneously with prolactin (PRL) (0.4 ng/ml) to quiescent Nb2 lymphoma cells. Cell counts were made 48 hours later. The following abbreviations were used for the compounds tested: HQH-1-45-28, 3-[N-2-Chloro,6-fluorophenylacetylaminopiperidine]-2,6-dione; HQH-1-44-11, 3-[N-2-fluorophenylacetylaminopiperidine]-2,6-dione; HQH-1-41-27, 3-[N-2,6-difluorophenylacetylaminopiperidine]-2,6-dione; HQH-1-36-36, 3-[N=4-hydroxyphenylacetylaminopiperidine]-2,6-dione; HQH-1-51-29, 3-[N-4-fluorophenylacetylaminopiperidine]-2,6-dione; and HQH-2-48-30, 3-[N-3-fluorophenylacetylaminopiperidine]-2,6-dione.

A comparison of the inhibitory effects of the piperidinediones on PRL stimulation of proliferation in the NB2 lymphoma cell line (0.4 ng/ml) is provided in FIG. 2. As illustrated, p-OH-A10 provided the greatest inhibition of lymphoma cell growth. Compounds HQH-1-45-28 (3-[N-2-chloro,6-fluoro-phenylacetylaminopiperidi]-2,6-dione), HQH-1-51-29 (3-[N-4-fluorophenylacetylaminopiperidine]-2,6-dione), and HQH-2-48-30, (3-[N-3-fluorophenylacetylaminopiperidine]-2,6-dione) also significantly inhibited proliferation of these cells. The 2-fluorophenyl-A10 derivative and the 2,2-difluorophenyl-A10 derivative provided some inhibition of cell growth.

Example 6:

Inhibition of MCF=7 Cells

MCF-7 cells were grown in 5% fetal calf serum and 10 µg insulin/ml in MEM supplemented media. The cells were trypsinized during log phase growth and plated in T25 flasks at a cell number of 20,000 cells in 2 ml media. The cells were allowed to attach during a period of 48–72 hours. The media was then changed. The cell numbers were counted in control flasks and 1, 2.5, 5.0 and nM of A-10 or p-OH A-10 or control medium was added to each flask. Each experiment was done in triplicate. The media was changed at the end of 3 days and new aliquots of A-10 or p-OH A-10 or control media were added. After 3 more days of cell growth, the cells were detached from the culture flasks by adding ml of a solution of 0.05% trypsin and 0.02% EDTA. The cells were removed, and 20 ml isoton was added and counted in a Coulter Counter. The results are provided in Table 5 and illustrated in FIG. 3

TABLE 5

| | Inhibition of MCF-7 Cells CELL Number (Mean ± SEM) | | |
|---|---|---|---|
| Concentration (Mm) | Control | A-10 | P-OH-A-10 |
| 1.0 | 73759 ± 3309 | 67342 ± 261 | 48345 ± 4587 |
| 2.5 | 79699 ± 2951 | 54164 ± 7409 | 10120 ± 441 |
| 5.0 | 60513 ± 5015 | 44961 ± 1947 | 3383 ± 143 |
| 10.0 | 66675 ± 4308 | 27654 ± 2266 | — |

FIG. 3 is a graph indicating the inhibitory effect of 3-[N-4-hydroxyphenylacetylaminopiperidine]-2,6-dione (p-OH A10) and 3-[N-phenylacetylaminopiperidine]-2,6-dione (A10) on MCF-7 cells growing in log phase. As illustrated, at concentrations millimolar, p-OH-A10 is highly active in this cell line. For example, in the absence of test compound, MCF-7 cells growing in log phase reached a count of approximately 80,000. When grown in log phase under the same conditions but in the presence of 5 millimolar of A10, the cell count was reduced to slightly less than 40,000. When grown under the same conditions in the presence of 5 millimolar of p-OH-A10, the cell count was reduced to less than 10,000.

Example 7

Inhibition of Mouse Lymphoma (YAK) Cells

Cells were grown in Dalbecco's modified Eagle's media in log phase. These cell grow in suspension. Cells (22,263) were plated and treated with 4 mM quantities of various compounds. Cell numbers were counted after 72 hours of treatment by removing 100 µl aliquots and diluting the aliquot with 20 ml isoton. The DMSO:ETOH concentration in all samples was 0.53%. The results are provided in Table 6 and FIG. 4.

TABLE 6

| Inhibition of Mouse Lymphoma (YAK) Cells | |
|---|---|
| Compound | Cell Number (means ± SEM) |
| Control | 744800 ± 13952 |
| A-10 | 569467 ± 5126 |
| PAG | 543733 ± 7007 |

TABLE 6-continued

| Inhibition of Mouse Lymphoma (YAK) Cells | |
|---|---|
| Compound | Cell Number (means ± SEM) |
| PA | 574533 ± 11795 |
| 36-36 (p-OH-A-10) | 34533 ± 3034 |
| 51-29 | 517600 ± 6526 |
| 44-11 | 593867 ± 18360 |
| 48-30 | 506667 ± 35862 |
| 45-28 | 466400 ± 18616 |

FIG. 4 is a bar chart graph indicating the inhibition of mouse lymphoma (YAK) cell proliferation by cytostatic piperidinediones. As illustrated, p-OH-A10 provides dramatic inhibition of the growth of these hormone insensitive cells. Other 3-[N-phenylacetylaminopiperidine]-2,6-dione derivatives, including the 4-fluorophenyl, the 2-fluorophenyl, the 3-fluorophenyl, and the 2-chloro,6-fluorophenyl derivatives also provided some inhibition of cell growth.

IV. Preparation of Pharmaceutical Compositions and Mode of Administration

As stated above, the cytostatic piperidinediones of the present invention are useful in the study of proliferative diseases in animal models and in vitro cell cultures. The active compounds may also have a use in the treatment of neoplastic diseases in vivo. Pharmaceutical compositions including these active compounds can be prepared as described below.

The active compound or its pharmaceutically acceptable salt is included in the pharmaceutically acceptable carrier or diluent in an amount sufficient to exert an inhibitory effect on the growth of the target neoplastic or proliferative cell line in vitro or in vivo. The active materials can be administered by any appropriate route, for example, orally, parenterally, intravenously, intradermally, subcutaneously, intraperitoneally, or topically, in liquid or solid form.

The active compound is included in the pharmaceutically acceptable carrier in an amount sufficient to exert a therapeutically useful inhibitory effect on neoplastic or proliferative cells without serious toxic effect to healthy cells. By "inhibitory amount" is meant an amount of active ingredient sufficient to exert a cytostatic effect as measured by, for example, an assay such as that described in Examples 5 through 7, or measured by blood analysis or radiation analysis of the state of tumorigenesis in vivo.

The concentration of active compound in the drug composition will depend on absorption, inactivation, and excretion rates of the active compound as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions.

The active ingredient may be administered at once, or may be divided into a number of smaller doses to be administered at varying intervals of time.

If oral administration is desired, although not required, the compound may be provided in a composition that protects it from the acidic environment of the stomach. The compound can be orally administered in combination with an antacid formulation. The composition can also be administered in an enteric coating that maintains its integrity in the stomach and releases the active compound in the intestine.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials that modify the physical form of the dosage unit, for example, coatings of sugar, shellac, or other enteric agents.

The active compound or its pharmaceutically acceptable salt can be administered as a component of an elixir, suspension, syrup, wafer, chewing gum or the like. A syrup may contain, in addition to the active compounds, sucrose as a sweetening agent and certain preservatives, dyes, colorings and flavors.

The active compounds can also be mixed with other active materials that do not impair the desired action, or with materials that supplement the desired action, including other cytostatic or anticancer compounds.

Solutions or suspensions used for parenteral, intradermal, subcutaneous, or topical application can include the following components: a sterile diluent such as water for injection, saline solution, fixed oils, polyethylene glycols, lycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations are known to those skilled in the art. The materials can also be obtained commercially from Nova Pharmaceutical Corporation.

Liposomal suspensions are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Modifications and variations of the present invention, synthetic piperidinediones with cytostatic activity, will be obvious to those skilled in the art from the foregoing description. Such modifications and variations are intended to come within the scope of the appended claims.

We claim.

1. A compound of the formula:

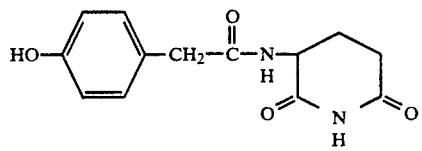

or its pharmaceutically acceptable salt.

2. A pharmaceutical composition comprising an effective cytostatic amount for humans of 3-2,6-dione in an pharmaceutically acceptable carrier.

3. The pharmaceutical composition of claim 2 wherein the pharmaceutical carrier is for topical administration.

4. The pharmaceutical composition of claim 2 where the pharmaceutical carrier is for systemic administration.

5. A method of inhibiting cell growth in a patient in need thereof comprising providing an effective amount of a compound of the formula

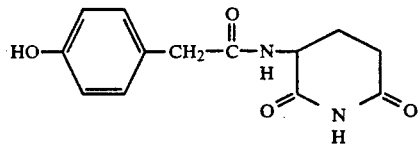

or its pharmaceutically acceptable salt.

* * * * *